United States Patent [19]

Robert et al.

[11] Patent Number: 5,689,053
[45] Date of Patent: Nov. 18, 1997

[54] *BRASSICA SP.* POLYGALACTURONASE GENE PROMOTER

[75] Inventors: Laurian S. Robert, Gatineau; Jean L. Gerster, Ottawa; Hai Ping Hong, Saskatoon, all of Canada

[73] Assignees: Her Majesty the Queen in right of Canada, as represented by Agriculture and Agri-Food; National Research Council of Canada, both of Canada

[21] Appl. No.: 577,463

[22] Filed: Dec. 21, 1995

[51] Int. Cl.⁶ .................... C12N 15/29; C12N 15/11; C12N 15/82; A01H 5/00
[52] U.S. Cl. .................... 800/205; 800/DIG. 26; 536/24.1; 435/172.3; 435/320.1; 435/419
[58] Field of Search .................... 800/205, DIG. 26; 536/24.1; 435/172.3, 240.4, 320.1

[56] References Cited

U.S. PATENT DOCUMENTS

| | | | |
|---|---|---|---|
| 5,086,169 | 2/1992 | Mascarennas | 536/27 |
| 5,412,085 | 5/1995 | Allen et al. | 536/24.1 |

OTHER PUBLICATIONS

Laurian S. Robert, et al., Isolation and characterization of a polygalacturonase gene highly expressed in *Brassica napus* pollen. *Plant Molecular Biology*, (1993) 23:1273–1278.

Rebecca L. Allen, et al., Molecular characterization of one of the maize polygalacturonase gene gamily members which are expressed during late pollen development. *The Plant Journal*, (1993) 3(2):261–271.

S.J. Tebbutt, et al., Deletion analysis of tobacco pollen–specific polygalacturonase promoter, *Sex Plant Reprod*, (1995) 308/1–308/5.

Hai Pint Hong, et al., Transformation of *Brassica napus* with the GUS Reporter Gene Under the Regulation of Tissue–Specific Promoters. Abstracts VIIIth International Congress of Plant Tissue and Cell Culture, Jun. 12–17, 1994.

*Primary Examiner*—Douglas W. Robinson
*Assistant Examiner*—Thomas Haas
*Attorney, Agent, or Firm*—Venable, Baetjer, Howard & Civiletti, LLP

[57] ABSTRACT

A *Brassica sp.* genomic clone containing a polygalacturonase gene promoter was isolated. This promoter directs high levels of transcription in the pollen. When the promoter was fused with the GUS gene and introduced into *B. napus* by Agrobacterium mediated transformation, this promoter controlled GUS expression in microspores and pollen in transgenic *B. napus* plants. Expression occurred between the late uninucleate microspore stage and the mature pollen grain stage. GUS activity was also identified in tapetal tissue at the binucleate microspore stage. There was no GUS expression in other tissues such as root, stem, leaf, sepal, petal or pistil. This promoter will be useful for the temporal and spatial control of endogenous gene expression in plants.

14 Claims, 4 Drawing Sheets

```
              10         20         30         40         50         60
               |          |          |          |          |          |
  1 AGACAGTATA CATAATTTAG AGAGAGTATT TTCAAGGTTT TAATCCAATT AAACATAATG
 61 ATGTTTTGAT AGTCTTTAAA AAGTATTTTC ACGTTTTCAA GATAAGATAA TAACTTTGAA
121 TTTTTTTAAT TCTTGTGTAG GCTCACGTTG ACATAGTACT TCCAAAGATT TTACACATCG
181 ACAACATAAA AAAAAACACT GGTATATATA TATATATATA TATATATATA TATATAGATG
241 TTTTTAATAT TGTGTCCCCC ATTAAAAACT TTTCAAAATC TGCCTCTGCT TCTCTCTGAG
301 CTATATACAT TATAGCCTTC ATATGTTGGT TTACGATAAA TCCGTCCAAC CGTATGTTTT
361 AAACATAATC TCTCTTCTTC ACTCATGTCA TTGGCTAACA TTGGCTAACA ATTAACCTGA
421 AAAATGTACG TATCATAAAA ATGCTATAAA CGTGCACGAG TAGAACAAGT CTTTCGTCTA
481 ATAATAAACC GCTAGTTTCT CAAAATTAAA TTAGCCTAGT AATTCCTTGA TAATTGGCCA
541 AACAATCTAA AAAACGAGAC GTTGAGAGAA AAATGGGTTA AACATATCTC CATTAAGGGC
601 ACTATATAAA GCAGCAGAGG CATAGCTAAA CTCTCATAAA ACAAAACAAA TAACAATAAA
661 AAACAAATAA AAAATAAATA AATAATG
```

FIG. 1

Sta 44/GUS-21 (multiple copies):

Sta 44/GUS-23 (multiple copies):

BRASSICA SP. POLYGALACTURONASE GENE PROMOTER

The present invention relates to plant gene promoters. Specifically this invention relates to a polygalacturonase gene promoter that directs high levels of transcription in the pollen.

BACKGROUND OF THE INVENTION

A cDNA clone (Sta 44) corresponding to a mRNA highly expressed in *Brassica napus* cv. Westar stamens, was isolated by differential screening and characterized. Northern blot and in situ analysis demonstrated this mRNA was synthesized in pollen and reached a maximum in trinucleate microspores (L. S. Robert et al., *Plant Molecular Biology*, 23:1273–1278, 1993). The Sta 44 cDNA clone was sequenced and through searches of protein databases, the sequence revealed substantial am/no acid sequence homology with polygalacturonase from different organisms.

A similar clone has been isolated from maize where it too has been found to be expressed during the late phase of pollen development (R. L. Allen et al., *Plant Journal*, 3:261–271, 1993). The corresponding maize pollen-specific polygalacturonase gene promoter has also been isolated (U.S. Pat. No. 5,412,085).

SUMMARY OF THE INVENTION

The present invention relates to plant gene promoters. Specifically this invention relates to a polygalacturonase gene promoter that directs high levels of transcription in the pollen.

In one embodiment of the present invention there is provided a *Brassica sp.* polygalacturonase gene promoter.

The present invention is also directed to a chimeric gene construct comprising the *Brassica sp.* polygalacturonase gene promoter of the present invention and the coding sequence of an exogenous gene.

The present invention is further directed to a method of conferring pollen-directed expression on a gene in a plant, comprising:
  operatively linking an endogenous gene, for which pollen-directed expression is desired, with a *Brassica sp.* polygalacturonase gene promoter of the present invention to produce a chimeric gene; introducing the chimeric gene into an appropriate vector; and introducing the vector into a plant capable of expressing the chimeric gene.

The present invention is further directed to transgenic plants containing a chimeric gene construct as described above.

BRIEF DESCRIPTION OF THE DRAWINGS

These and other features of the invention will become more apparent from the following description in which reference is made to the appended drawings wherein:

FIG. 1 is the nucleotide sequence of the 5' upstream region containing the promoter fragment of the *B. napus* polygalacturonase gene, which includes SEQ ID NO: 1. The ATG start is underlined. This promoter fragment, up to position 647, was used with the GUS fusion construct.

DESCRIPTION OF PREFERRED EMBODIMENT

Figure 2:
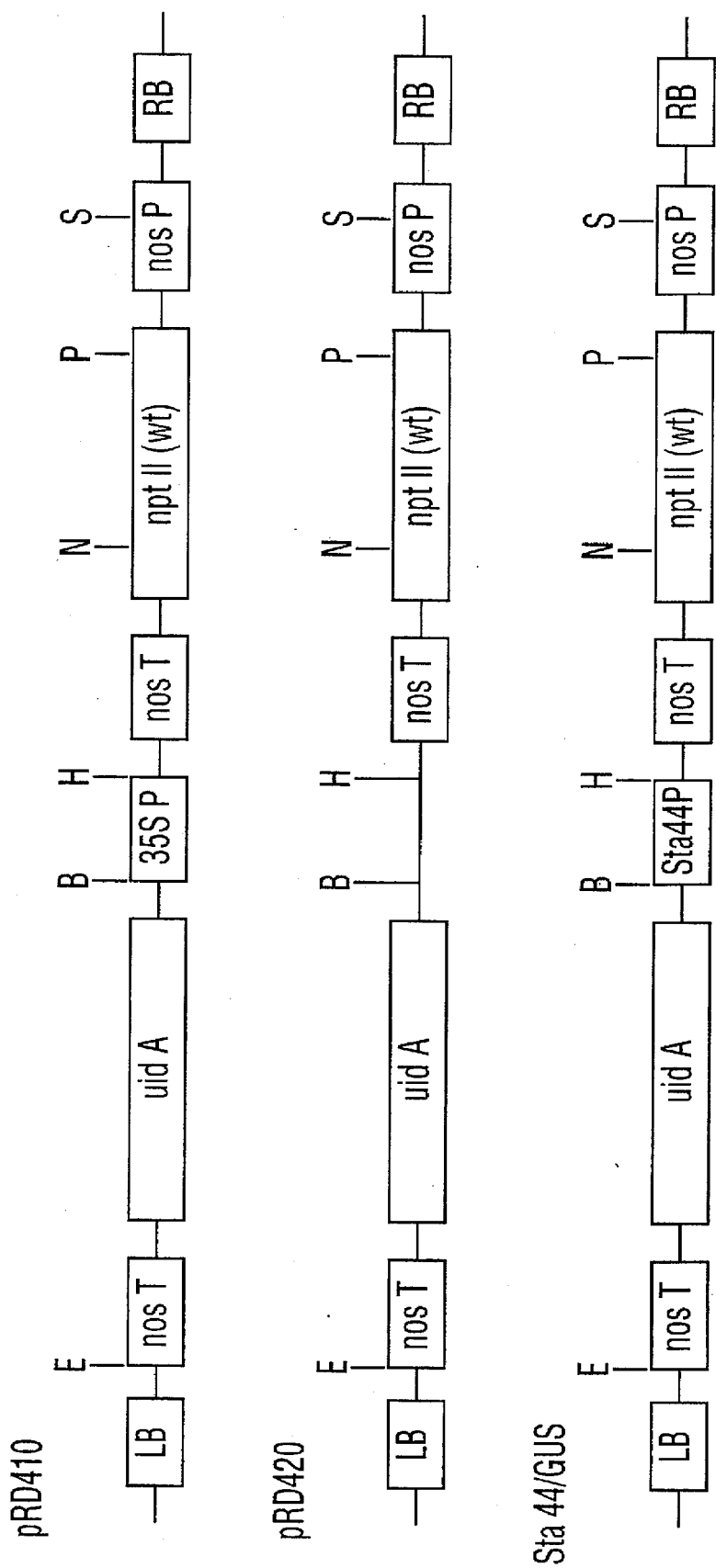
FIG. 2 shows the construct of plasmids pRD410, pRD420 and Sta 44/GUS (pRD 420 containing the Sta 44 promoter).
Figure 3A:
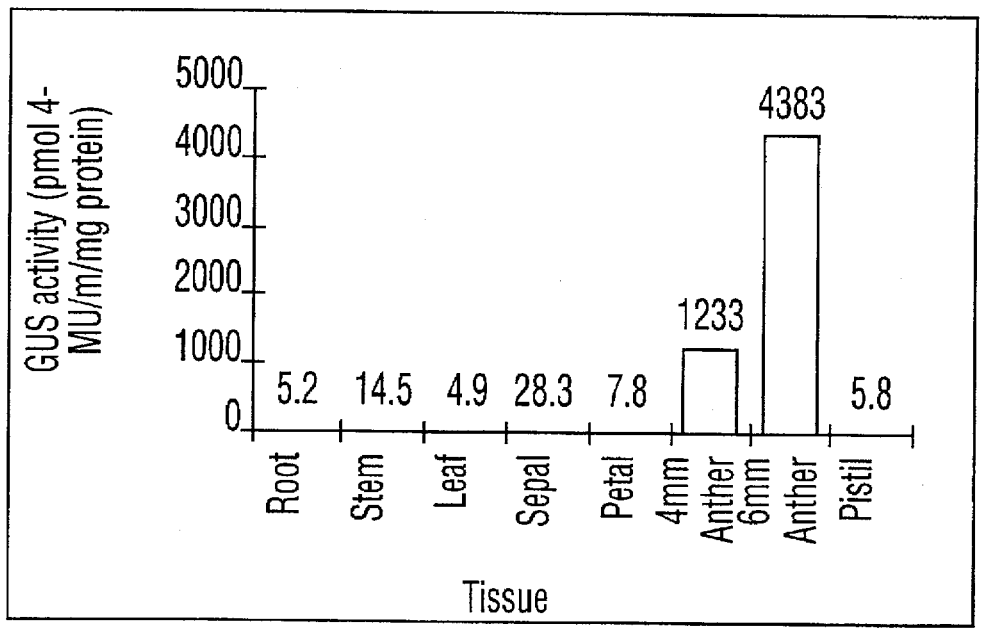
FIG. 3 shows the fluorometric GUS activity in a Sta 44/GUS transgenic plant, wherein 3A is transgenic plant number 7 with a double insertion; 3B is transgenic plant number 20 with a multiple insertion; 3C is transgenic plant number 21 with a multiple insertion and 3D is transgenic plant number 23 with a multiple insertion.
Figure 3B:
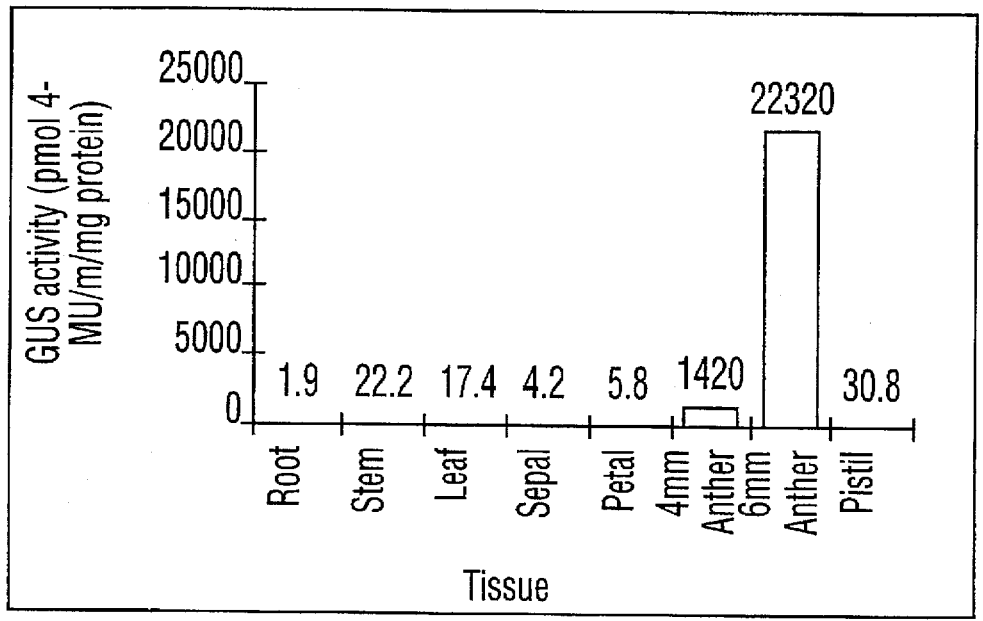
Figure 3C:
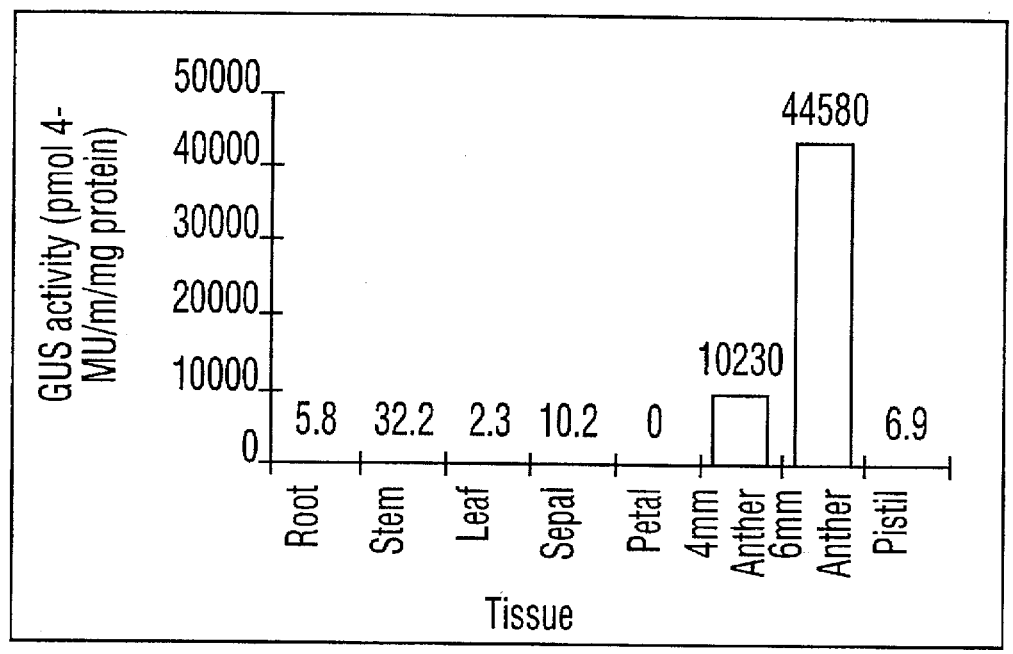
Figure 3D:
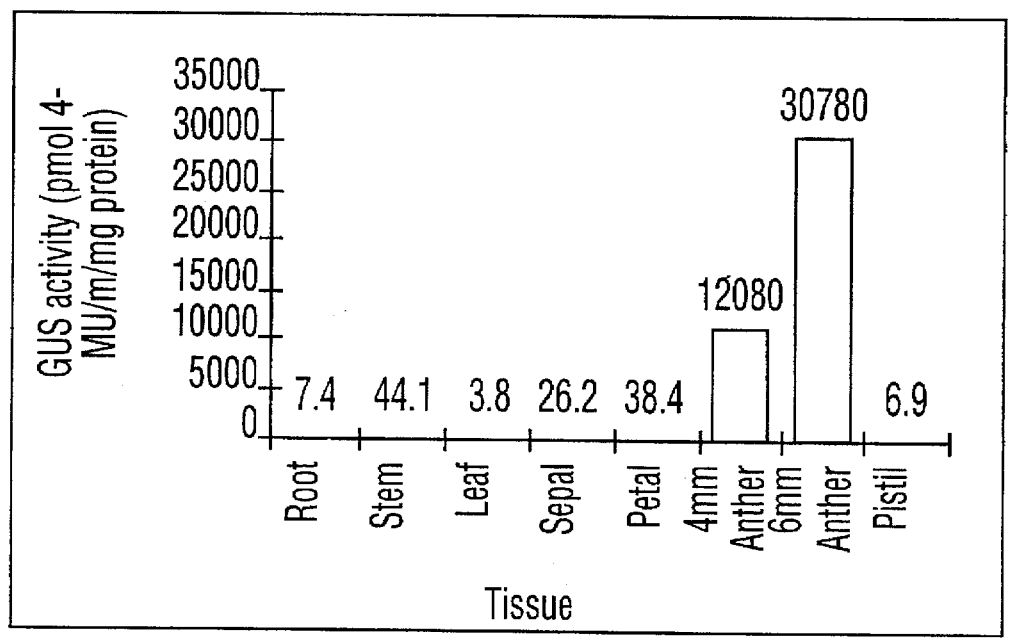

The present invention relates to plant gene promoters. Specifically this invention relates to a polygalacturonase gene promoter that directs high levels of transcription in the pollen.

In the context of this disclosure, the term "promoter" or "promoter region" refers to a sequence of DNA, usually upstream (5') to the coding sequence of a structural gene, which controls the expression of the coding region by providing the recognition for RNA polymerase and/or other factors required for transcription to start at the correct site.

The present invention is directed to a promoter which facilitates the spacial and temporal expression of a gene in pollen. Specifically, the present invention is directed to a promoter isolated from *Brassica sp.* The promoter, in its native form, controls the expression of a polygalacturonase gene in *Brassica sp.* pollen.

One embodiment of the present invention is directed to a promoter isolated from *Brassica napus*. Substantial homology has been demonstrated between *B. napus* and other species of Brassica. Thus, the present invention is not limited to the promoter isolated from *Brassica napus*, but includes within its scope the corresponding promoter from other species of Brassica.

The present invention is further directed to a chimeric gene construct containing a gene of interest wherein said gene is operatively linked to the promoter of the present invention. Any exogenous gene can be used and manipulated according to the present invention to result in the pollen-directed expression of said exogenous gene.

Many genes important to pollen development could be used according to the present invention to cause male sterility for the purpose of hybrid seed production for example. The Sta 44 pollen polygalacturonase gene itself could be used. If this gene is critical to pollen development, expressing an antisense version or a sense version (in this case the inhibition would occur by co-suppression) of this gene in the pollen could reduce the Sta 44 gene activity and result in male sterility. Genes coding for products which would disrupt the development of the pollen could also be used to cause male sterility according to the present invention. For example, the promoter of the present invention could be fused to a gene encoding the diphteria toxin A chain (Thorsness et al., Dev Biol, 143:173–184, 1991) or a RNAse (for example Barnase from *Bacillus amyloliquefaciens*; Hartley, Gene, 53:11–20). The promoter could also be useful for example, to target the expression of genes which are toxic to insects or pests which consume pollen or genes which alter the composition of pollen, such as its nutritional composition.

In the context of the present disclosure, the term "operatively linked" is meant to mean that the various components of the chimeric gene construct of the present invention are positioned so as to ensure the proper transcription, or transcription and translation of the desired sequence. For example, a chimeric gene could be constructed by replacing the *B. napus* polygalacturonase coding region of the genomic clone Sta 44G2 with the complete or partial coding region of another gene in the sense or antisense orientation. A chimeric gene could also be constructed by replacing a specific promoter with the *B. napus* polygalacturonase promoter in such a way as to allow the proper transcription, or transcription and translation of a particular sequence in anthers.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can also be used.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be of a variety of origins, both natural and synthetic. Translational initiation regions may be provided from the source of the transcriptional initiation region, or from the structural gene. The sequence can also be derived from the promoter selected to express the gene, and can be specifically modified So as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase, uid A), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Any plant species can be modified, according to the present invention, to include the chimeric gene construct to provide pollen-directed expression of an exogenous gene.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); and Grierson and Corey, *Plant Molecular Biology*, 2nd Ed. (1988). The present invention further includes a suitable vector comprising the chimeric gene construct.

When specific sequences are referred to in the present invention, it is understood that these sequences include within their scope sequences that are "substantially homologous" to said specific sequences. Sequences are "substantially homologous" when at least about 80%, preferably at least about 90% and most preferably at least about 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389). Such substantially homologous sequences have been found in other *Brassica* species (L. S. Robert et al., *Plant Molecular Biology*, 23:1273–1278, 1993).

The specific sequences, referred to in the present invention, also include sequences which are "functionally equivalent" to said specific sequences. In the present invention functionally equivalent sequences refer to sequences which although not identical to the specific sequences provide the same or substantially the same function. Sequences that are functionally equivalent include any substitution, deletion or addition within the sequence. With reference to the present invention functionally equivalent sequences will also direct the expression of an exogenous gene to the pollen.

While this invention is described in detail with particular reference to preferred embodiments thereof, said embodiments are offered to illustrate but not limit the invention.

EXAMPLES

Example 1

Isolation of the *B. napus* Genomic Clone
Containing the Pollen-Expressed Polygalacturonase
Gene The spring *B. napus* cv. Westar genomic library was constructed in the vector λ DashII as recommended by the manufacturer (Stratagene). Genomic DNA was extracted from nuclei (Jofuku and Goldberg, 1988, in *Plant Molecular Biology*:a practical approach, 37–66), partially digested with Sau 3A and size fractionated (9–20 kb) as described in Unit 5.3-*Current Protocols in Molecular Biology* (1987). The genomic library (300,000 plaque forming units) was probed with the [$^{32}$P]oligolabelled Sta 44 cDNA clone (Robert et al., *Plant Mol. Biol.*, 23:1273–1278, 1993). A genomic clone, Sta 44G2, containing a member of the *B. napus* pollen-expressed polygalacturonase gene family was isolated and characterized.

A Hind III/Pst I fragment containing the 5' upstream region of the Sta 44G2 gene was subcloned into the Hind III/Pst I sites of pGEM 4Z (Promega) and used to generate the Sta 44 promoter fragment. The sequence of this promoter fragment is shown in FIG. 1 (SEQ ID NO: 1). The sequence of this promoter fragment as found in its native form, is as depicted in FIG. 1. For a reference, the initiation codon ATG from the polygalacturonase is also shown and underlined in FIG. 1. The initiator codon is not included within SEQ ID NO: 1. For the polygalacturonase gene promoter-GUS fusion constructs, the promoter fragment used is that as shown in FIG. 1, up to the nucleotide position 647, as shown by the arrow in FIG. 1. This promoter fragment (647 bp) was obtained by the polymerase chain reaction (PCR) using the primer Sta 44G(2)-1 5'-TATGGATCCGTTTTGTTTTATGAGAG-3' (SEQ ID NO: 2) which is complementary to sequence −37 to −53 bp upstream of the translational start ATG in Sta 44G2 (to which a Bam HI site was added) and the SP6 promoter primer found in the pGEM 4Z plasmid. Amplifications were performed in a 100 µl volume containing 1X Taq DNA polymerase buffer (Promega)/1.5 mM MgCl$_2$/0.2 mM dNTPs/250 ng of each primer/1 ng of the subcloned DNA. Following 5 min. at 95° C., 2.5 U of Taq polymerase was added and 35 cycles of 1 min. at 95° C., 1 min. at 42° C., 2 min. at 72° C. were performed and followed by a 10 min. extension at 72° C. The Sta 44 promoter/PCR fragment was sequenced and then subcloned as a Bam HI/Hind III fragment upstream of the GUS gene of the binary vector pRD 420 (FIG. 2) for use in plant transformation.

Example 2

Agrobacterium-mediated Plant Transformation with Sta 44/GUS

Plasmid pRD 410 was used as a positive control and has a GUS (β-glucuronidase) gene under the control of the CaMV 35S promoter and for transformed plant selection the NPT II (neomycin phosphotransferase II) gene under the control of the nos (nopaline synthase) promoter (R. S. S. Datla et al., *Gene*, 211:383-384 (1992)). Plasmid pRD 420 was used as a negative control and is similar to pRD 410, but lacks the CaMV 35S promoter. Plasmid Sta 44/GUS contains the 647 bp fragment from the pollen-expressed polygalacturonase gene (Sta 44G2). These plasmids are depicted in FIG. 2.

The recombinant plasmid DNAs were introduced directly into the *Agrobacterium tumefaciens* strain GV3101:pMP90 following the protocol supplied with Pharmacia Agrobacterium cells (product: #27-1535). To prepare the Agrobacterium competent cells, 5 ml of YEP media (10 g yeast extract, 10 g peptone, 5 g sodium chloride (NaCl) per liter, pH 7.0) with 150 µg/ml rifampicin (chromosomal marker) and 100 µg/ml gentamycin (pTi marker) was inoculated with a loopful of a glycerol stock of *Agrobacterium tumefaciens* GV 3101:pMP90 and cultured at 28° C. by shaking at 250 rpm approximately 15 h. The next day, 2 ml of the overnight culture was added to 50 ml of fresh YEP media and grown at 28° C. to reach an O.D. of 0.5–1.0 (at 600 nm). The culture was then chilled on ice for 10 min. and centrifuged at 5,000 rpm in a Sorvall SS34 for 5 min. The cells were resuspended in 1 ml cold 20 mM CaCl$_2$. These competent cells were dispensed into prechilled 1.5 ml Eppendorf tubes in 100 µl aliquots and frozen at −80° C. until further use.

The Agrobacterium cells were transformed as follows. One µg of uncut plasmid DNA (pRD 410, pRD 420 or Sta 44/GUS) in water was added to 100 µl of Agrobacterium competent cells and incubated on ice for 30 min. The cells were then frozen in liquid nitrogen and thawed quickly at 37° C. for 5 min. and 1 ml of YEP medium was added to the cell/DNA mixture and incubated at 28° C. for 2 h with gentle shaking (100 rpm). Cells were then centrifuged in a microfuge for 30 s, the supernatant was poured out and the pellet resuspended in the remaining supernatant (50–100 µl). The resuspended cells were spread onto a YEP plate with 150 µg/ml rifampicin, 100 µg/ml gentamycin and 50 µg/ml kanamycin and incubated at 28° C. for 2–3 days.

Plasmid DNA from individual Agrobacterium colonies was digested with Eco RI and Hind III or Hind III and Bam HI, respectively, along with RNase A at 37° C. for 2 h and analyzed by gel electrophoresis in 0.8% agarose. Colonies which contained recombinant plasmid were selected and grown overnight in 5 ml AB minimal medium with 50 µg/ml kanamycin and 50 µg/ml gentamycin. The overnight culture was centrifuged at 4500 rpm for 15 min. and the cells were resuspended in 1 ml of double distilled water or 10 mM MgSO$_4$ (with 7% DMSO stocks could be kept at −70° C. for further use).

Agrobacterium-mediated transformation of *B. napus* cv. Westar was performed according to the method of Moloney et al., *Plant Cell Reports*, 8:238–242, (1989), with minor modifications. Seeds were sterilized by brief wetting in 95% ethanol then 70% commercial bleach (Javex) with a drop of detergent (Tween 20) for 15 min. with occasional agitation; 0.025% mercuric chloride with a drop of Tween 20 for 10 min. and finally rinsed well with sterile distilled water at least 3 times. Thirty to forty seeds were plated on ½ strength hormone-free MS medium (SIGMA) with 1% sucrose in 15×60 mm petri dishes. They were then placed, with the lid removed, into a sterilized Majenta GA7 jar and were kept at 25° C., with 16 h light/8 h dark and a light intensity of 70–80 µE.

Cotyledons were excised from 4-day old seedlings by gently grasping both petioles just above the point where they join the hypocotyl. The cut edge was dipped briefly into an overnight Agrobacterium culture containing the recombinant plasmid DNA and 50–60 cotyledons were placed in each plate containing Medium I [4.57 g/l M.M.O. (GIBCO BRL), 3% sucrose, 4.5 mg/l benzyl adenine (BA), 0.7% phytagar (GIBCO BRL), pH 5.8]. After three days of cocultivation explants were transferred to plates containing Medium II [4.57 g/l M.M.O., 4.5 mg/l BA, 3% sucrose, 0.7% phytagar, pH 5.8. Carbenicillin (500 mg/l). After 7 days the explants were transferred to plates containing Medium III [4.57 g/l M.M.O., 4.5 mg/l BA, 3% sucrose, 0.7% phytagar, pH 5.8, carbenicillin (500 mg/l) and kanamycin (20 mg/l) were added after autoclaving]. The plates were cultured for 2–3 weeks at which time green shoot buds could be identified; these were directly transferred to glass jars containing Medium IV [4.44 g/l MS/B5 (SIGMA), 0.1 mg/l NAA, 3% sucrose, 0.7 phytagar, pH 5.8, (500 mg/l) carbenicillin and (50 mg/l) kanamycin]. Once a good root system had developed, the plantlets were removed from jars, most of the agar was removed from the roots and then transferred to moist potting soil.

Transformants were screened to confirm the presence of the T-DNA by using a [$^{32}$P]oligolabelled fragment of the GUS gene using standard Southern hybridization procedures (Sambrook et al., in Molecular Cloning (A Laboratory Manual), 2nd Ed., Cold Spring Harbor Laboratory (1989).

The 647 bp Sta 44 promoter was sufficient to direct the tissue-specific expression of the GUS gene in developing *B. napus* anthers. The Sta 44 promoter expressed exclusively in the anther, and most abundantly in the pollen of developing anthers. No GUS activity was detected in roots, stem, leaf, sepal, petal, or pistil at flowering. The negative control plants which were transformed with the promoterless/GUS vector pRD 420 did not give any GUS expression within 1–2 days of incubation, however, after 2–3 days of X-Gluc staining, a couple of plants showed weak GUS expression in some root regions.

The positive control plants which contain the CaMV 35S/GUS vector pRD 410 showed varying levels of GUS expression among six transgenic plants. It was generally found that GUS expression occurred in most tissues under the control of the 35S promoter, although there were some minor differences in the degree of GUS expression at different stages.

In *B. napus* plants grown under equivalent conditions, the length of the flower bud is a good indicator for the developmental stage of the microsporocytes. Most microspores are at the same stage of development in anthers of flower buds of the same length (Albani et al., *Plant Molecular Biology*, 15:605–622 (1990)). Six transgenic plants containing the Sta 44/GUS chimeric construct were selected and assayed histochemically for GUS activity in the floral organs following the methods of Jefferson et al., *Plant Molecular Biology Reporter*, 5:387–405 (1987). The flower organs (sepal, petal, stamen and pistil) of a series of different bud sizes (2–6 mm buds and open flower) from each of the six plants as well as whole root segments and hand sections of stem and leaf were dissected and placed in a 24-well tissue culture plate containing 300–500 µl of reaction buffer. The reaction buffer contained 1 mM X-Gluc (5-bromo-4-chloro-3-indolyl-β-D-glucuronicacid, Sigma) in 0.1M sodium phosphate, pH 7.0, 10 mM EDTA, 0.1% Triton X-100 and 0.5 mM potassium ferricyanide, 0.5 mM potassium ferrocyanide. The staining reaction was carried out at room temperature for 1 h to overnight depending on the intensity of staining. GUS activity was scored as +, ++ or +++ depending on the intensity of GUS staining. In all cases, GUS expression was only observed in anthers and not in other organs. GUS expression increased progressively during anther development and was most abundant at microspore maturation (5–6 mm) and in pollen grains (Table 1).

TABLE 1

Temporal expression of Sta 44/GUS in anthers of transgenic *B. napus*

| Transgenic line no. | 2 mm | 3 mm | 4 mm | 5 mm | 6 mm | open flower |
|---|---|---|---|---|---|---|
| 1 | + | + | ++ | +++ | +++ | +++ |
| 7 | – | + | ++ | +++ | +++ | +++ |
| 20 | ++ | ++ | ++ | +++ | +++ | +++ |
| 21 | + | + | ++ | +++ | +++ | +++ |
| 23 | – | ++ | +++ | +++ | +++ | +++ |
| 28 | – | – | +++ | +++ | +++ | +++ |

+++ strong activity;
++ high activity;
+ low activity;
– no activity

To verify the cellular localization of the Sta 44 promoter activity, cryosections of buds from approximately 1 mm in length to approximately 6 mm length, and also from open flowers were examined in a histochemical assay. Anthers from transgenic plants at different developmental stages were mounted in cryomold (25×20×5 mm) using frozen tissue embedding media (Tissue-Tek II OCT compound) and sectioned at –20° C. using a 2800 Frigo cut cryostat II (Reichert-Jung, FRG). Sections were picked up and melted on a slide, and then stained with X-Gluc (same as above) at 37° C. for half an hour to one hour, then sections were carefully washed with ethanol and directly mounted for microscopy (Leitz Microscope). GUS activity was determined in anthers at various stages of male gametophytic development. These studies further confirmed the developmental pattern of expression. GUS expression was detected in the uninucleate microspores (approximately 3 mm bud); then increased sharply by the binucleate microspore stage. At this stage Sta 44 promoter-driven GUS activity was detected both in microspores and tapetal cells (approximately 4 mm bud). As binucleate microspores developed, the tapeturn tissue degenerated (approximately 5 mm bud). Maximal GUS expression was detected in microspores at the trinucleate microspore stage (6 mm). Similarly high levels of expression were maintained in mature pollen grains (results not shown).

A fluorometric quantitative assay for GUS expression was performed as follows. Approximately 10–15 µl extracts from sepal, petal, anther and carpel, and 80–100 µl extracts from root, stem and leaf, were added separately to pre-warmed Eppendorf tubes containing 1 ml of assay buffer (extraction buffer containing 1 mM 4-methyl umbelliferyl glucuronide) and incubated at 37° C. A time course was produced by removing 300 µl aliquots and adding them to 2.7 ml stop buffer (0.2M $Na_2CO_3$). The incubation was carried out at 37° C. for zero, 30 min. and 60 min. for roots, stems and leaves; zero, 15 min. and 30 min. for sepals, petals, anthers and carpels.

The fluorometer was calibrated by reading a series of concentrations of 4-methyl umbelliferone (from 1 to 100 µM) under different filter and magnification conditions, with excitation at 254–650 nm, emission at 225–650 nm on a Tuner Fluorimeter (Model 112). The rate of increase in fluorescence of samples was measured under the same conditions. A standard of $10^{-4}$ mM 4-MU was used for comparison with each sample reading and stop buffer was used to adjust fluorimeter after each sample measurement.

The specific activity of the GUS enzyme in the extracts was calculated as pmol 4-MU formed per min. per mg total protein added. GUS activity was estimated from the average of the two individual samples and each sample with two repeats. The standard deviation was calculated based on these four repeats.

The quantitative assay of GUS expression in transgenic plants containing the pollen Sta 44/GUS fusion is shown in FIG. 3, 3A, 3B, 3C and 3D. High levels of GUS activity were detected only in extracts from anthers of all these plants. Essentially no GUS activity was found in other vegetative or floral organs, although extracts of stem tissue showed GUS activity 6.6- to 20-fold above the background levels, however, it was 302- to 1385-fold lower than that detected in anthers. Independent transformants showed approximately a 10-fold variation in the level of GUS activity, presumably due to insertional position effects frequently observed in transgenic plants. The maximum level of GUS activity was found in anthers from flower buds of about 6 mm, a finding consistent with the histochemical observations.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

---

The embodiments of the invention in which an exclusive property or privilege is claimed are defined as follows:

1. An isolated and purified *Brassica sp.* polygalacturonase promoter, which directs transcription in pollen wherein said promoter has a nucleotide sequence which is at least 80% homologous to SEQ ID NO: 1.

2. The promoter according to claim 1, wherein the promoter has a nucleotide sequence of SEQ ID NO: 1.

3. The promoter according to claim 1, wherein the *Brassica sp.* is *Brassica napus*.

4. A chimeric gene construct comprising a *Brassica sp.* polygalacturonase gene promoter and a coding sequence of an exogenous gene, wherein said promoter directs transcription of the exogenous gene in the pollen and has a nucleotide sequence which is at least 80% homologous to SEQ ID NO: 1.

5. The chimeric gene construct according to claim 4, wherein the *Brassica sp.* is *Brassica napus*.

6. A vector comprising the chimeric gene construct of claim 4.

7. The vector according to claim 6 wherein the *Brassica sp.* is *Brassica napus*.

8. The vector according to claim 6, wherein said promoter has a nucleotide sequence of SEQ ID NO: 1.

9. A method of conferring pollen-directed expression of a gene in a plant, comprising:

operatively linking an endogenous gene, for which pollen-directed expression is desired, with a *Brassica sp.* polygalacturonase gene promoter to produce a chimeric gene;

introducing the chimeric gene into an appropriate vector; and introducing the vector into a plant capable of expressing the chimeric gene;

wherein the promoter has a nucleotide sequence at least 80% homologous to SEQ ID NO: 1.

10. The method according to claim 9 wherein the *Brassica sp.* is *Brassica napus*.

11. The method according to claim 9, wherein said promoter has a nucleotide sequence of SEQ ID NO: 1.

12. A transgenic plant containing the chimeric gene construct of claim 4.

13. The transgenic plant according to claim 12, wherein the *Brassica sp.* is *Brassica napus*.

14. The transgenic plant according to claim 13, wherein said promoter has a nucleotide sequence of SEQ ID NO: 1.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 684 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 1:

```
AGACAGTATA  CATAATTTAG  AGAGAGTATT  TTCAAGGTTT  TAATCCAATT  AAACATAATG      60
ATGTTTTGAT  AGTCTTTAAA  AAGTATTTTC  ACGTTTTCAA  GATAAGATAA  TAACTTTGAA     120
TTTTTTTAAT  TCTTGTGTAG  GCTCACGTTG  ACATAGTACT  TCCAAAGATT  TTACACATCG     180
ACAACATAAA  AAAAACACT   GGTATATATA  TATATATATA  TATATATATA  TATATAGATG     240
TTTTAATAT   TGTGTCCCCC  ATTAAAAACT  TTTCAAAATC  TGCCTCTGCT  TCTCTCTGAG     300
CTATATACAT  TATAGCCTTC  ATATGTTGGT  TTACGATAAA  TCCGTCCAAC  CGTATGTTTT     360
AAACATAATG  TCTCTTCTTC  ACTCATGTCA  ATTTCATAAG  TTGGCTAACA  ATTAACCTGA     420
AAAATGTACG  TATCATAAAA  ATGCTATAAA  CGTGCACGAG  TAGAACAAGT  CTTTCGTCTA     480
ATAATAAACC  GCTAGTTTCT  CAAAATTAAA  TTAGCCTAGT  AATTCCTTGA  TAATTGGCCA     540
AACAATCTAA  AAAACGAGAC  GTTGAGAGAA  AAATGGGTTA  AACATATCTC  CATTAAGGGC     600
ACTATATAAA  GCAGCAGAGG  CATAGCTAAA  CTCTCATAAA  ACAAAACAAA  TAACAATAAA     660
AAACAAATAA  AAAATAAATA  AATA                                               684
```

( 2 ) INFORMATION FOR SEQ ID NO: 2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

```
TATGGATCCG  TTTTGTTTTA  TGAGAG                                              26
```